United States Patent [19]

Ponsford et al.

[11] 4,256,638
[45] Mar. 17, 1981

[54] PROCESS FOR MANUFACTURE OF 9-AMINO-9-DEOXYCLAVULANATES

[75] Inventors: Roger J. Ponsford, Dorking; Thomas T. Howarth, Ewhurst, both of England

[73] Assignee: Beecham Group Limited, Great Britain

[21] Appl. No.: 942,156

[22] Filed: Sep. 14, 1978

Related U.S. Application Data

[62] Division of Ser. No. 731,928, Oct. 13, 1976, abandoned.

[30] Foreign Application Priority Data

Oct. 13, 1976 [GB] United Kingdom ............... 41887/76

[51] Int. Cl.³ .................... C07D 498/04; C07B 29/00
[52] U.S. Cl. .................................. 260/245.3; 542/420
[58] Field of Search ..................... 260/307 FA, 245.3; 542/420

[56] References Cited

U.S. PATENT DOCUMENTS 3,925,363  12/1975  Cama ................................ 260/239.1
4,051,132  9/1977  Firestone ............................. 544/20

OTHER PUBLICATIONS

Morrison et al.–"Organic Chemistry"–Allyn & Bacon, Inc.–1959–p. 484.

Primary Examiner—Mark L. Berch
Attorney, Agent, or Firm—Jacobs & Jacobs

[57] ABSTRACT

The compounds of the formula (II):

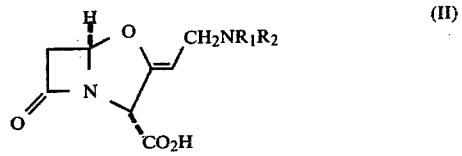

and salts and esters thereof wherein $R_1$ is an inert organic group of up to 14 carbon atoms and $R_2$ is an inert organic group of up to 16 carbon atoms, the group $NR_1R_2$ containing up to 22 carbon atoms, are antibacterial agents able to enhance the effectiveness of penicillins and cephalosporins against certain β-lactamase producing bacteria.

17 Claims, No Drawings

PROCESS FOR MANUFACTURE OF 9-AMINO-9-DEOXYCLAVULANATES

CROSS-REFERENCE

This is a division of Ser. No. 731,928 filed Oct. 13, 1976 now abandoned.

The present invention relates to antibacterial agents which also possess β-lactamase inhibitory activity, to their preparation and to pharmaceutical compositions containing them.

Belgian Pat. No. 827,926 discloses inter alia clavulanic acid, which is the compound of the formula (I):

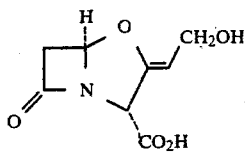

and its salts and esters. Clavulanic acid was shown to be a useful antibacterial agent which possesses β-lactamase inhibitory properties which allowed it to enhance the antibacterial effectiveness of penicillins and cephalosporins against many gram-negative and gram-positive bacteria. We have now discovered a further group of compounds that exhibit antibacterial and β-lactamase inhibitory activity but which have a different spectrum of activity than clavulanic acid and its salts.

The present invention provides compounds of the formula (II)

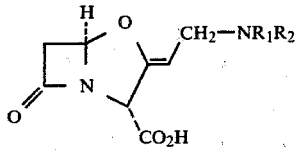

and salts and esters thereof wherein $R_1$ is an inert organic group of up to 14 carbon atoms and $R_2$ is an inert organic group of up to 16 carbon atoms, the $NR_1R_2$ group containing up to 22 carbon atoms.

When used herein the term 'inert organic group' means any organic group that is itself stable and which does not contain any functional groupings which cause rupture of the β-lactam ring of the compound of the formula (II). Such groups do not include highly electron withdrawing groups situated in a manner which prevents the amine of the formula (III)

$$HNR_1R_2 \qquad (III)$$

from being sufficiently basic to form a salt of the carboxyl group of the compound of the formula (I) nor do they contain substituents that render the amine of the formula (III) unstable. Normally $R_1$ and $R_2$ are such that the conjugate acid of the amine of the formula $H_2NR_1R_2$ has a pKa of from 7.0 to 11.2 and preferably has a pKa of 8 to 10.

More suitably $R_1$ contains not more than 8 carbon atoms. More suitably $R_2$ contains not more than 14 carbon atoms. Most suitably the $NR_1R_2$ group contains not more than 16 carbon atoms. Suitable values for $R_1$ include hydrocarbon groups (such as alkyl, alkenyl, phenylalkyl, phenylalkenyl or the like) optionally inertly substituted by halogen, OH, $OR_3$, $O.CO_2R_3$, $SR_3$, $COR_3$ or the like whererin $R_3$ is a hydrocarbon group of up to 8 carbon atoms.

One group of particularly suitable values for $R_1$ is that of the sub-formula (a):

(a)

wherein $R_4$ is a hydrogen atom or a $C_{1-4}$ alkyl group, $R_5$ is a hydrogen atom or a $C_{1-4}$ alkyl group and $R_6$ is an optionally substituted phenyl group.

More suitably $R_4$ is a hydrogen atom. More suitably $R_5$ is a hydrogen atom.

When used herein the term "optionally substituted phenyl Group" means a phenyl group or a phenyl group substituted by halogen, OH, $OR_7$, $OCOR_7$, $CO_2R_7$ or $COR_7$ where $R_7$ is a hydrocarbon group of up to 7 carbon atoms and more suitably the term means a phenyl group or a phenyl group substituted by halogen, $C_{1-4}$ alkyl, $C_{1-4}$ alkoxyl or hydroxyl.

Particularly suitable groups of the sub-formula (a) include the benzyl, methoxybenzyl and chlorobenzyl groups, especially the benzyl group.

A further group of particularly suitable values for $R_1$ is that of the sub-formula (b):

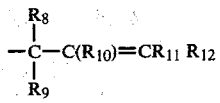

wherein each of $R_8$ to $R_{11}$ is independently a hydrogen atom or a $C_{1-4}$ alkyl group and $R_{12}$ is a $C_{1-4}$ alkyl group or an optionally substituted phenyl group or a hydrogen atom.

More suitably each of $R_8$ to $R_{11}$ is independently a hydrogen atom at or a methyl group. More suitably each of $R_9$ to $R_{11}$ is independently a hydrogen atom. More suitably $R_{12}$ is a hydrogen atom or a $C_{1-4}$ alkyl group.

Yet another particularly suitable group of values for $R_1$, is that of the sub-formula (c)

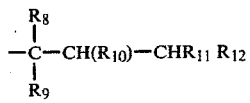

(c)

wherein $R_8$ to $R_{12}$ are as defined in relation to sub-formula (b).

Particularly suitable groups $R_2$ include those of the sub-formula (a), (b) and (c) previously described as suitable for $R_1$. The group $R_2$ need not have the same value as the group $R_1$ but it is sometimes convenient for it to be so.

Other particularly suitable groups $R_2$ include those of the sub-formula (d):

$$-CHR_{13}R_{14} \qquad (d)$$

wherein $R_{13}$ is a hydrogen atom or a $C_{1-4}$ alkyl group and $R_{14}$ is an alkyl group of 1–14 carbon atoms optionally substituted by OH, $OR_{16}$, $OCOR_{16}$ or $COR_{16}$ where $R_{16}$ is a hydrocarbon group of up to 8 carbon atoms.

When $R_{13}$ is a hydrogen atom it is preferred that $R_{14}$ is not a methyl group.

Particularly suitable groups of the sub-formulae (d) include the isopropyl, 2-hydroxyethyl, 2-hydroxypropyl, ethyl, 2-acetoxyethyl, 2-methoxyethyl and the like group.

Suitable esters of the formula include those of the formulae (IV) and (V):

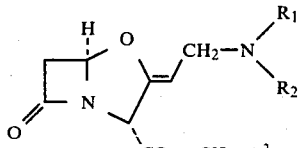 (IV)

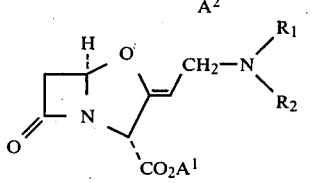 (V)

and acid addition salts thereof wherein $R_1$ and $R_2$ are as defined in relation to formula (II) and $A^1$ is an alkyl group of 1-8 carbon atoms optionally substituted by halogen or a group of the formula $OA^4$, $OCOA^4$, $SA^4$, $SO_2A^4$ wherein $A^4$ is a hydrocarbon group of up to 6 carbon atoms; $A^2$ is a hydrogen atom, an alkyl group of up to 4 carbon atoms or a phenyl group optionally substituted by halogen or by a group $A^5$ or $OA^5$ where $A^5$ is an alkyl group of up to 6 carbon atoms; and $A^3$ is a phenyl group optionally substituted by halogen or by a group $A^5$ or $OA^5$ where $A^5$ is an alkyl group of up to 6 carbon atoms.

Suitable acid addition salts include those formed with pharmaceutically acceptable acids which are known to be suitable for forming salts with esters of penicillins or cephalosporins which contain a basic group.

A further suitable group of esters are those which are readily in-vivo hydrolysable which include, but are not limited to, those of the formulae (V) and (V):

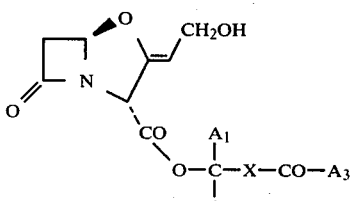 (V')

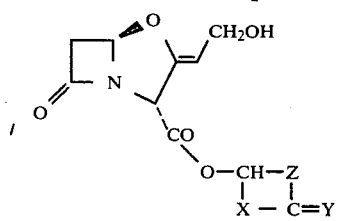 (VI')

wherein $A_1$ is a hydrogen atom, alkyl, aryl or aralkyl group; $A_2$ is a hydrogen atom or methyl group; $A_3$ is an alkyl, aryl or aralkyl group; X is oxygen or sulphur; Y is oxygen or sulphur and Z is a divalent organic group. Esters of the formulae (V') and (VI') which fairly readily release the clavulanic acid into the blood stream after administration include those wherein $A_1$ is a hydrogen atom, $A_2$ is a hydrogen atom or a methyl group and $A_3$ is a methyl, ethyl, propyl, butyl, benzyl, or phenyl group and those wherein X is oxygen, Y is oxygen and Z is $-CH_2CH_2-$, $-CH:CH-$,

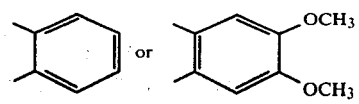

When used in conjunction with the preceeding formula the term 'alkyl' includes alkyl of up to six carbon atoms; the term 'aryl' includes phenyl, naphthyl or phenyl substituted by an inert substituent such as a fluorine or chlorine atom or a methyl or methoxyl group or the like; when used herein the term 'aralkyl' means an alkyl group substituted by an aryl group.

Particularly suitable esters of the formulae (V') and (VI') include those of the formulae (VII') and (VIII'):

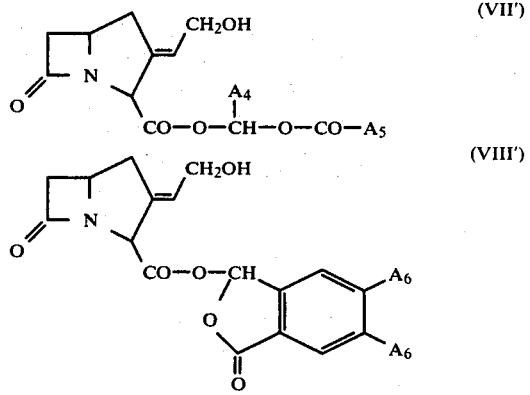

$A_4$ is a hydrogen atom or a methyl group, $A_5$ is a methyl, t-butyl or phenyl group and $A_6$ is a hydrogen atom or a methoxyl group.

Many esters of clavulanic acid differ from analagous esters of penicillins or cephalosporins in that they show an enhanced tendency to hydrolyse to clavulanic acid under mild conditions. Thus, for example, simple alkyl esters such as the methyl ester slowly hydrolyse to clavulanic acid in water buffered to pH7. Esters which undergo some hydrolysis under mild conditions are included within the formula (IX'):

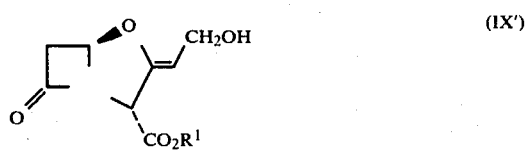

wherein $R^1$ is a hydrocarbon group of 1-9 carbon atoms optionally substituted by halogen, lower alkoxy, hydroxyl or optionally salted basic groups of the formula $NR^2R^3$ wherein $R^2$ is a hydrogen atom or a lower alkyl group, $R^3$ is a hydrogen atom or a lower alkyl group or is attached to $R^2$ so that $NR^2R^3$ is a 5- or 6-membered ring.

When used with reference to formula (IX') the term 'lower' means that the group contains 1-4 carbon atoms.

Suitably groups $R^1$ include alkyl and aralkyl groups optionally substituted by halogen, methoxyl, hydroxyl or salted $NR^2R^3$ groups wherein $R^2$ is a methyl or ethyl group and $R^3$ is a methyl or ethyl group or is joined to $R^2$ so that $NR^2R^3$ is a pyrrolidine, piperidine or morpholine group.

Most suitably alkyl groups $R^1$ are straight chain groups of up to 6 carbon atoms optionally substituted by one methoxyl, hydroxyl, salted $NR^2R^3$ group or one chlorine, bromine or iodine atom or by a $CCl_3$ or $CF_3$ group. Suitable in-vivo hydrolysable esters include phthalidyl, acetoxymethyl, pivaloyloxymethyl, α-acetoxyethyl, ethoxycarbonyloxymethyl, α-ethoxycarbonyloxyethyl and the like esters.

When non-esterified, the compounds of this invention are normally salted. Such salts are preferably zwitterionic salts of the formula (VI).

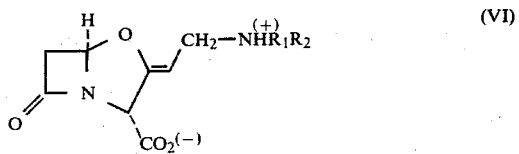
(VI)

Other salts of the compounds of formula (II) include those with pharmaceutically acceptable salting ions such as the sodium, potassium, calcium, magnesium, aluminium, ammonium, and substituted ammonium ions and also those with pharmaceutically acceptable acids. These other salts are not a preferred feature of the invention. From the preceeding statements it will be realised that certain particularly suitable compounds of this invention are of the formulae (VII)-(IX)

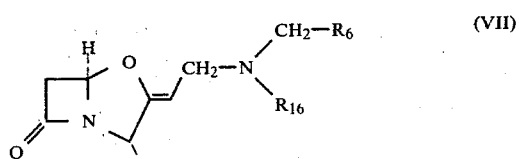
(VII)

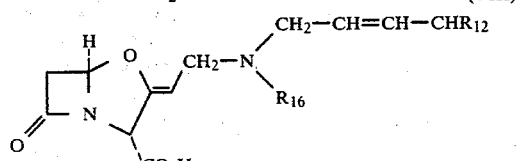
(VIII)

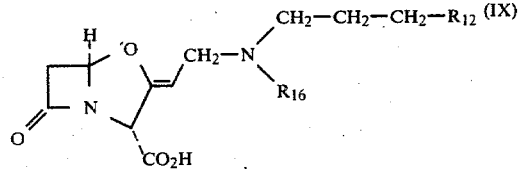
(IX)

and in-vivo hydrolysable esters thereof wherein $R_6$ and $R_{12}$ are as described in relation to sub-formulae (a), (b) and (c) and $R_{13}$ is a $CH_2R_6$, $CH_2CH{:}CHR_{12}$, $CH_2$—$CH_2$—$CH_2$—$R_{12}$ or $CHR_{13}R_{14}$ group where $R_{13}$ and $R_{14}$ are defined as in relation to sub-formula (d).

Compounds within formulae (VII) can be particularly effective in inhibiting β-lactamases produced by gram-positive bacteria. Compounds within formulae (VII) and (IX) are envisaged as useful for their broad spectrum of β-lactamase inhibition.

The present invention provides a process for the preparation of the compounds of the formula (II) and salts and esters thereof which process comprises the reaction of an amine of the formula (III)

$$HNR_1R_2 \qquad (III)$$

wherein $R_1$ and $R_2$ are as defined in relation to formula (II), and a compound of the formula (X).

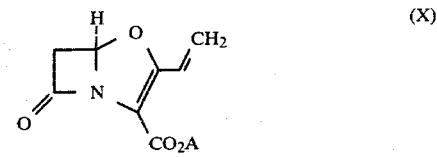
(X)

where $CO_2A$ is an ester group and thereafter if desired converting the thus formed compound into the corresponding carboxylic acid or a salt.

The diene of the formula (X) may be formed before the reaction with the amine of the formula (III) or it may be prepared in situ. Suitable methods of preparing the diene in situ include the displacement of sulphate or carboxylate moiety from a compound of the formulae (XI) or (XII)

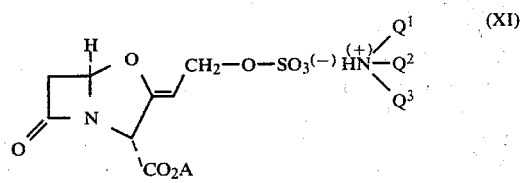
(XI)

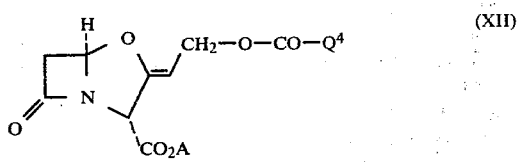
(XII)

wherein A is as defined in relation to formula (X), $Q^1$, $Q^2$ and $Q^3$ are groups such that $NQ^1$, $Q^2$, $Q^3$ is a tertiary amine and $Q^4$ is an organic group.

Suitably the reaction of the amine of the formula (III) with the compound of the formula (X), (XI) or (XII) will take place in an aprotic solvent such as acetonitrile, dimethylformamide or other similar solvent at a non-extreme temperature, for example—10° to 50° C., more usually—5° to 25° C. and conveniently within the range 0° to 20°.

Suitably one or more of $Q^1$, $Q^2$ and $Q^3$ is a $C_{1-6}$ alkyl group such as a methyl or ethyl group.

Suitably $Q^4$ is a $C_{1-6}$ alkyl, benzyl, dichloromethyl or like group.

It is frequently advantageous to use the preformed diene ester of the formula (X) rather than to generate it in situ.

When a compound of the formula (XI) or (XII) is used in the process of this invention a certain degree of direct displacement of the leaving group by the amine may take place but it is believed that in general most and possibly effectively all of the desired compound is produced via the diene.

The present invention also provides a process for the preparation of acids of the formula (II) and the carboxylate salts thereof which process comprises the de-esterification of a corresponding ester of the compound of the formula (II) and if desired simultaneously or subsequently salting the carboxyl group.

De-esterification may be brought about by conventional mild methods such as hydrogenation or mild basic hydrolysis.

Suitable hydrogenolysable esters of the compound of the formula (II) include benzyl and like esters. Such esters may be cleaved by hydrogenation using a low or medium pressure of hydrogen, for example about 1 atmosphere, at an approximately ambient temperature, for example about 12°-20° C., in a conventional inert solvent, for example ethanol.

If a base is present a basic salt maybe formed. Normally no base is present and the zwitterionic salt results.

Suitable base hydrolysable esters include acetoxymethyl, phthalidyl and the like ester which undergo hydrolysis when maintained in an aqueous medium at a pH of 7 to 8.5. Such reactions can occur rapidly, for example in 10-60 minutes. Most suitably such reactions take place in a solvent which is water or water together with an organic solvent such as tetrahydrofuran. The reaction usually occurs sufficiently rapidly at 5°-20° C. The pH may be maintained at the correct level by the careful addition of base. This is generally a less suitable method of cleaving the ester than hydrogenolysis.

Compounds of the formula (II) where both or one of $R_1$ and $R_2$ is a group of the sub-formula (c) as hereinbefore described may be prepared by the reduction of a corresponding compound containing a corresponding group of the sub-formula (b). Such reactions are normally effected by hydrogenation in the presence of a transition metal catalyst in conventional manner.

The present invention also provides pharmaceutical compositions which comprise a compound of this invention and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegration and the like in accordance with conventional pharmaceutical practice in the manner well understood by those skilled in the art of formulating antibiotics.

Injectable or infusable compositions of salts of a compound of the formula (II) are particularly suitable as high tissue levels of a compound of the formula (II) can occur after administration by injection or infusion. Thus, one preferred composition aspect of this invention comprises a salt of a compound of the formula (II) in sterile form.

Unit dose compositions comprising a compound of the formula (II) or a salt or ester thereof adapted for oral administration form a further preferred composition aspect of this invention.

The compound of the formula (II) or its salt or ester may be present in the composition as sole therapeutic agent or it may be present together with other therapeutic agents such as a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, cephalothin, cefazolin, cephalexin, cefoxitin, cephacetrile, cephamandole nafate, cephapirin, cephradine, 4-hydroxycephalexin, cefaparole, cephaloglycine, and other well known pencillins and cephalosporins or pro-drugs therefore such as hetacillin, metampicillin, 4-acetoxyampicillin, the acetoxymethyl, ethoxycarbonyloxymethyl, pivaloyloxymethyl or phthalidyl esters of benzylpenicillin, ampicillin, amoxycillin or cephaloglycine or the phenyl, tolyl or indanyl α-esters or carbenicillin or ticarcillin or the like. Such compounds are frequently used in the form of a salt or hydrate.

Naturally if the penicillin or cephalosporin present in the composition is not suitable for oral administration then the composition will be adapted for parenteral administration.

When present in a pharmaceutical composition together with a β-lactam antibiotic, the ratio of a compound of the formula (II) or its salt or ester present to β-lactam antibiotic present may vary over a wide range of ratios, for example 10:1 to 1:3 and advantageously may be from 5:1 to 1:2, for example, 3:1 to 1:1.

The total quantity of antibacterial agents present in any unit dosage form will normally be between 50 and 1500 mg and will usually be between 100 and 1000 mg.

Compositions of this invention may be used for the treatment of infections on inter alia, the respiratory tract, the urinary tract and soft tissues and mastitis in cattle.

Normally between 50 and 3000 mg of the compounds of the invention will be administered each day of treatment but more usually between 100 and 1000 mg of the compounds of the invention will be administered per day, for example as 1-6 doses, more usually 2-4 doses.

The penicillin or cephalosporin in synergistic compositions of this invention will normally be present by up to or at approximately the amount at which it is conventionally used.

Particularly favoured compositions of this invention will contain from 150-1000 mg of amoxycillin, ampicillin or a pro-drug therefore and from 50-500 mg of a compound of the formula (II) or a salt or in-vivo hydrolysable ester thereof and more suitably from 200-500 mg of amoxycillin, ampicillin or a pro-drug therefore and from 50-250 mg of a compound of the formula (II) or a salt or in-vivo hydrolysable ester thereof.

The materials present in such compositions may be hydrated if required, for example ampicillin trihydrate or amoxycillin trihydrate may be employed. The weights of the antibiotics in such compositions are expressed on the basis of antibiotic theoretically available from the composition and not on the basis of the weight of pro-drug.

EXAMPLE 1 Benzyl 3-(2-dibenzylaminoethylidene)-7-oxo-1-azabicylo[3.2.0-]heptane-2-carboxylate (e2)

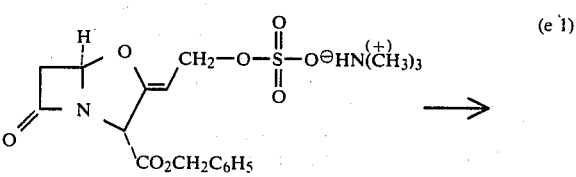

-continued

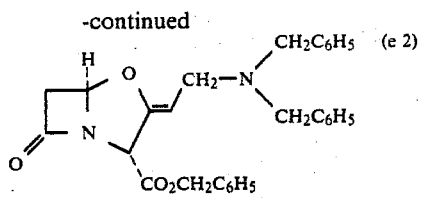

Crude benzyl clavulanyl sulphate trimethylammonium salt (e1) (500 mg) in freshly distilled dimethylformamide (5 ml) was treated with a solution of dibenzylamine (450 mg) in dimethylformamide (2 ml) dropwise over 15 minutes. The reaction was stirred at room temperature for 2 hours and diluted with ethyl acetate/petroleum ether (b.p. 60–80) 1/1 (50 ml). The solution was chromatographed directly on silica gel to yield as the first eluted product benzyl dibenzylaminodeoxy clavulanate (e2) as a light yellow oil (84 mg.) Re-chromatography afforded pure (e2) as a colourless oil (38 mg.)

The preparation of (e1) is described in German Patent Application No. 2616087 and United States Patent application Ser. No. 675,273

N.m.r. (CDCl$_3$): 3.00 (1H, d, J=17 Hz, 6$\beta$-CH); 3.20 (2H, d,J=8 Hz), C$\underline{H}_2$N); 3.52 (1H, dd, J=17 Hz, 6$\alpha$-C$\underline{H}$); 3.57 [4H, s, N(C$\underline{H}_2$Ph)$_2$]; 4.84 (1H, br.t., J=8 Hz, olefinic C$\underline{H}$); 5.13 (iH, br.s., 3-C$\underline{H}$); 5.25 (2H, s, CO$_2$C$\underline{H}_2$Ph); 5.69 (1H, d, J=2.5 Hz, 5-C$\underline{H}$); 7.41$\delta$(15H, s, aromatic protons).

When the compound prepared by the method of Example 1 was tested against certain enzymes by the $\beta$-lactamase inhibition assay described in Belgian Patent No. 827926 the following $I_{50}$ values were obtained:

| Enzyme | Approximate $I_{50}$ (in mg/ml) |
| --- | --- |
| E. coli JT4 | 0.02 |
| E. coli JT10 | 0.24 |
| Klebsiella aerogenes AE70 | 0.40 |
| Staphylococcus aureus (Russell) | 0.06 |
| Pseudomonas aeruginosa | 0.14 |
| Citrobacter mantio | 0.15 |

EXAMPLE 2 Methyl 3-(2-dibenzylaminoethylidene)-7-oxo-4-1-azabicyclo[3,2,0]2-carboxylate

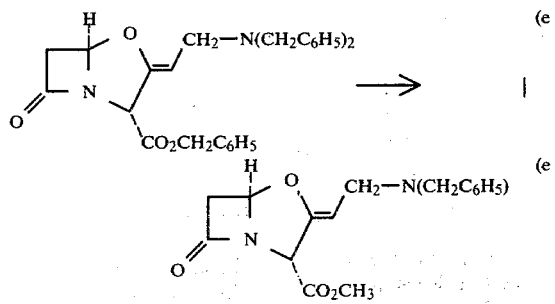

The compound (e2) (100 mg) in tetrahydrofuran (5 ml) was hydrogenated at ambient temperature and pressure over 10% Pd/C (50 mg) for one hour. The solution was filtered through keirselguhr, the solvent evaporated, the residue dissolved in ethylacetate (10 ml) and extracted with water (4×10 ml). The water was evaporated to yield a gum which was dissolved in methanol (5 ml) and treated with excess/diazomethane at 0° C. Evaporation of the solvent and chromatography yield the desired compound (methyl dibenzylamino deoxyclavulanate (e3) as a colourless gum.

i.r. (CHCl$_3$) 1800, 1755, 1700 cm$^{-1}$ n.m.r. (CDCl$_3$) 2.94 (1H,d,J=17 Hz, 6$\beta$-C$\underline{H}$); 3.17 (2H, d, J=7 Hz, =CH-C$\underline{H}_2$); 3.41 (1H, dd, J=17 Hz, J$^1$=2.5 Hz, 6$\alpha$-C$\underline{H}$); 3.53 (4H,s, N[C$\underline{H}_2$C$_6$H$_5$]$_2$); 3.74 (3H, s, CO$_2$C$\underline{H}$); 4.78 (1H,brit, J=7 Hz, =C$\underline{H}$-CH$_2$) 5.01 (1H, br. s, 3-C$\underline{H}$); 5.60 (1H, d, J=2.5 Hz, 5-C$\underline{H}$) 7.30 $\delta$(10H,s N[CH$_2$ C$_6$H$_5$]$_2$ [$\alpha$]$^{25}$=0.4° (C=0.81; MeOH).

EXAMPLE 3 Benzyl N-benzyl-N-2-hydroxyethylamino-deoxyclavulanate

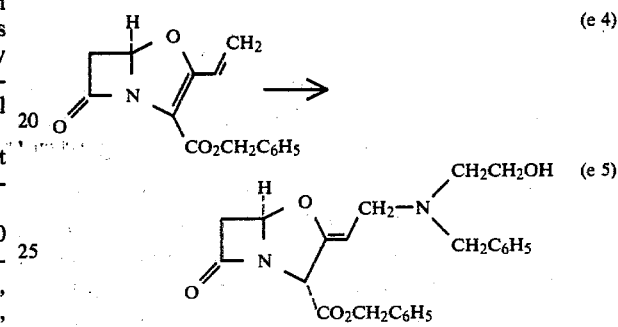

Clavudiene benzyl ester (0.5 g) in acetonitrile (10 ml) was cooled to 0° C., N-benzyl-2-hydroxyethylamine (0.36 g) was added and the reaction mixture stirred for 2½ hours. Ethyl acetate (100 ml) was added and the mixture evaporated to low volume. The residue was subjected to column chromatography using ethyl acetate as eluent. The product, was isolated in low yield had an ir spectrum (liquid film) as follows: 3400 (broad, —OH), 1800 ($\beta$-lactam C=O), 1740 (ester C=O), 1700 (C=C), 695 cm$^{-1}$ (aromatic protons). The n.m.r. spectrum was consistent with the desired product (e5).

EXAMPLE 4 Benzyl N-benzyl-N-isopropylamino deoxyclavulanate

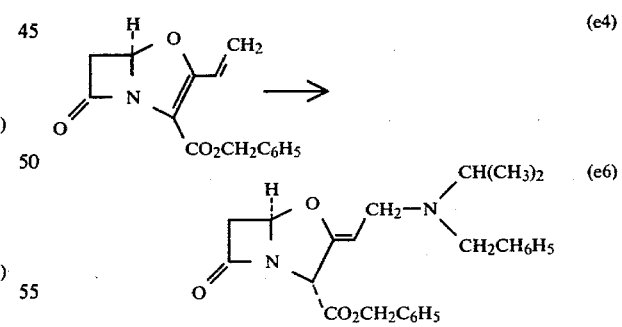

The ester(e4)(0.5 g) in acetonitrile (10 ml) was cooled in ice-water. N-iso propylbenzylamine (0.39 g, 1.3 moles) was added with stirring. The reaction mixture was allowed to warm to room temperature and stirred for 3 hours. Ethyl acetate (100 ml) was added, and the solution evaporated to low bulk in vacuo. The residue was subjected to column chromatography on silica gel using cyclohexane and ethyl acetate as eluents. The product (e6) was eluted after the unreacted diene. It had Ir spectrum (liquid film) as follows: 1803, ($\beta$-lactam C=O) 1845 (ester C=O) 1700 (C=C) 695 cm$^{-1}$ (aromatic protons). The n.m.r. spectrum was consistent with the desired product EXAMPLE 5 Benzyl dibenzylaminodeoxyclavulanate

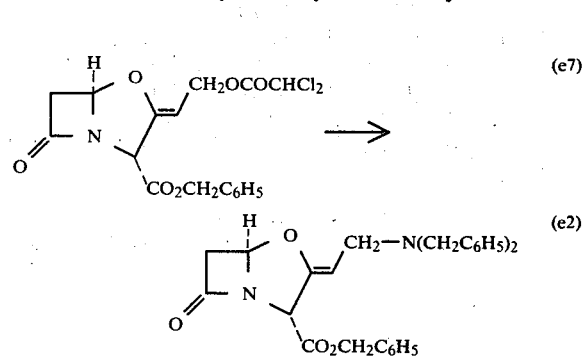

Benzyl dichloroacetylclavulanate (e7) (0.8 g) was dissolved in dry dimethylformamide and cooled to 0° C., treated with dibenzylamine (768 μl; 0.004 mol) in dry dimethylformamide (4 ml) over 15 minutes, the temperature being maintained at 0° C. The resulting yellow solution was stirred at 0° for 2½ hours and a room temperature for 4 hours. Ethylacetate was added (100 ml) and the solution washed with water (3×25 ml), dried and evaporated. The product was purified by fast gradient elution on silica gel using ethyl acetate/cyclohexane as the eluting solvent (Yield 0.33 g).

n.m.r. (CDCl$_3$)2.92 (d, IH,J 17 Hz, 6β-$\underline{H}$) 3.12 (2H, d, J 8 Hz, =CH C$\underline{H}_2$N) 3.38 (IH,dd,J=17 Hz, J$^1$2.5 Hz, 6α-$\underline{H}$) 3.46 (4H,s,N(C$\underline{H}_2$ Ph)$_2$ 4.72 (IH, dt, J 8 Hz,=C$\underline{H}$ CH$_2$)5.01 (IH,bs, C$\underline{H}$ CO$_2$B$_z$) 5.12 (2H, s CO$_2$CH$_2$Ph) 5.53 (IH,d, J 2.5 Hz, 5-C$\underline{H}$) 7.22 (15H,S, aromatic-H)

EXAMPLE 6 Benzyl dibenzylaminodeoxyclavulanate

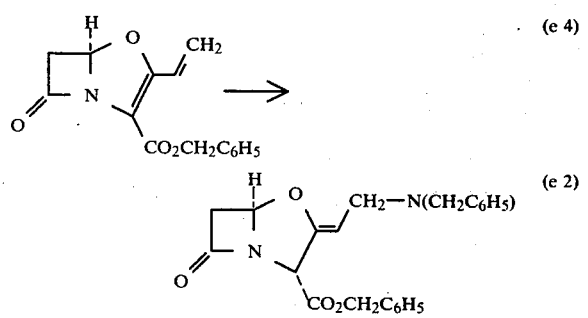

The diene (e4) (271 mg) in dry acetonitrile (4 ml) at 0° C. was treated with dibenzylamine (197 mg) in dry acetonitrile (2 ml) over 5 minutes. The reaction mixture was stirred at 0° C. for 2 hours and at room temperature for 2 hours. The solvent was removed by evaporation and the residue dissolved in ethyl acetate, washed with water, dried evaporated and fractionated on silica-gel to yield the desired product (e2) which was purified by chromatography.

EXAMPLE 7 Benzyl N-benzyl-9-(dl-2-hydroxypropylamino-9-deoxyclavulanate

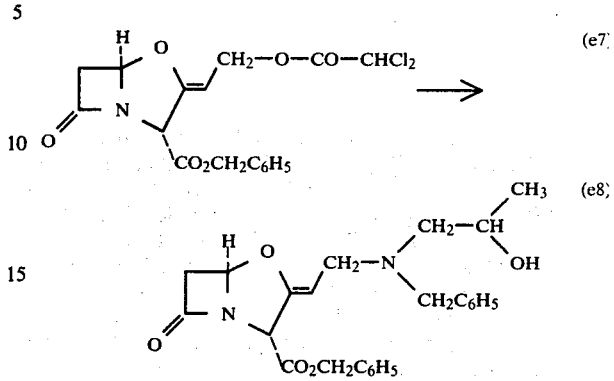

Benzyl dichloroacetylclavulanate (e7) (0.8 g) in dry dimethylformamide (20 ml) was cooled to 0° C. and a solution of dl-1-benzylamino-2-propanol (0.65 g) in dry dimethylformamide was added slowly. Stirring was continued for 4 hours at 0° C.

A more polar component was formed (thin layer chromatograph) and worked up as described in example 5 and chromatographed to give the desired product (e8) (0.16 g)

i.r. (film)3450, 1808, 1750, 1700 cm$^{-1}$
n.m.r. (CDCl$_3$) 0.9

OH
(3H, d, J 6Hz, CH. CH$_3$) 2.32 (2H, dd,

J 7Hz, J$^1$ 2Hz, CH$_2$ CH. CH$_3$)
OH 2.97 (1H, dd, J 17.5 Hz, J$^1$ 1.5 Hz 6β-$\underline{H}$) 3.17 (2H, d, J 7 HZ, =CH.C$\underline{H}_2$) 3.56 (1H, dd, J 17.5 HZ, J$^1$ 2.5 HZ, 6α$\underline{H}$) 3.48 (2H, s N C$\underline{H}_2$Ph) 4.75 (1H, bt, J 7 Hz, =C$\underline{H}$ CH$_2$) 5.1 (1H, s, C-3) 5.18 (2H,s, CO$_2$ CHph) 5.63 (1H, d,J 2.5 Hz 5-$\underline{H}$) 7.21, 7.3 (10H, s, aromatic-$\underline{H}$)

EXAMPLE 8 Benzyl diallylaminodeoxyclavulanate

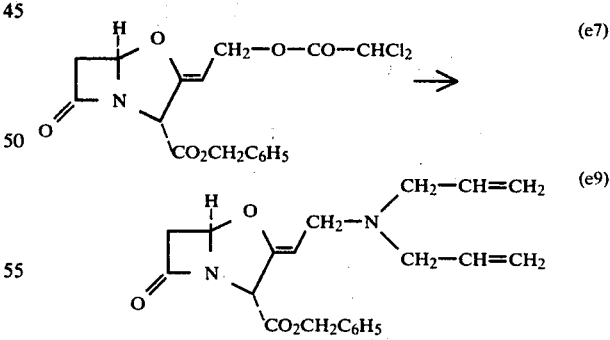

Benzyl dichloroacetylcalvulanate (e7) (0.4 g) was dissolved in dry dimethylformamide (7 mls) and cooled to 0° C. A solution of diallylamine (246 μl; 0.002 mol) in dry dimethylformamide (2 ml) was added the temperature was maintained at 0° C. The solution was stirred for 2 hours at 0° and at 15° for 15 minutes. Ethyl acetate (75 ml) was added and the solution washed with water (2×35 ml) dried and evaporated. The more polar product was isolated by column chromatography on silica gel and was obtained as a yellow oil (0.18 g);

i.r.(film) 1804, 1755, 1695, 1640 cm$^{-1}$.

n.m.r. (CDCl$_3$), 2.96 (1H,d, J 17 Hz, 6β-H) 2.97 (4H, d, J 6 Hz, N(CH$_2$ CH=CH$_2$) 3.13 (2H, d, J 7 Hz, =CH CH$_2$N<), 3.41 (1H,dd,J' 2.5 Hz 6α-H) 4.68 (1H,dt, J 7 Hz, =CH CH$_2$)4.97–5.13 (5H, m,3-CH and N[CH$_2$CH=CH$_2$]$_2$), 5.13 (2H, s superimposed on broad m, CO$_2$CH$_2$Ph), 5.62 (1H, d, J 2.5 Hz, 5-H), 5.75 (2H, m, N[CH$_2$CH=CH$_2$]), 7.3 (5H, s, CH$_2$Ph).

EXAMPLE 9 p-Methoxybenzyl diallylaminodeoxyclavulanate

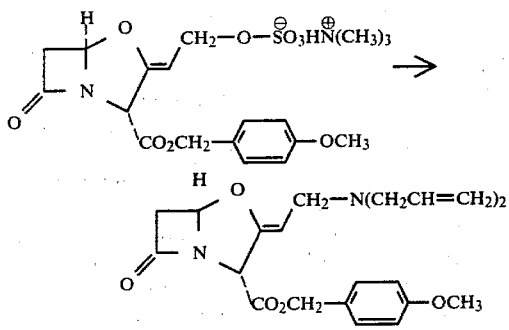

The sulphate (e10) (0.46 g) was dissolved in dry dimethylformamide (7 ml) and cooled to 0° C., diallylamine (0.175 g) in dry dimethylformamide (2 ml) was added slowly dropwise. The reaction mixture was stirred at 0° for 2 hours and worked up as in Example 5. Column chromatograph gave the product (e11) as a yellow oil.

EXAMPLE 10 9-(NN-dibenzylamino)-9-deoxyclavulanic acid

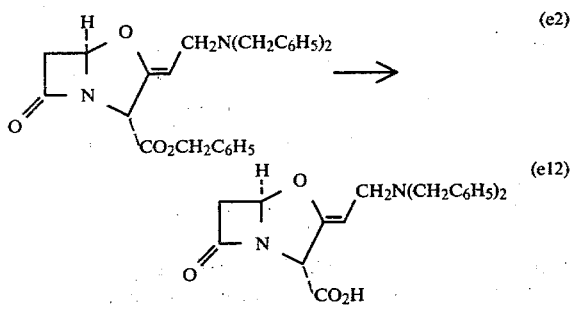

A solution of the benzyl ester (e2) (330 mg) in ethanol (20 ml) was hydrogenolysed at ambient temperature and pressure using 10% Pd/C (110 mg). The reaction was complete after 15 minutes.

The catalyst was filtered off and the filtrate evaporated, the crude product was dissolved in ethyl acetate (20 ml) and extracted with water (5×5 ml). The water was removed in vacuo to give the desired product (e12) as a pale yellow gum (yield 41%).

i.r. 3400 (b), 1800, 1700 (W), 1620 (b) cm$^{-1}$

EXAMPLE 11 Benzyl N-benzyl-N-norbornylaminodeoxyclavulanate

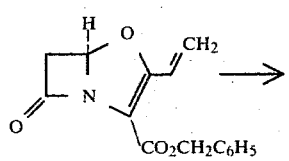

-continued

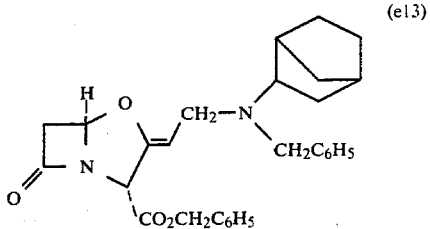

Clavudiene benzyl ester (0.5 g) in acetonitrile (10 ml) was treated at −15° with 2 (N-benzyl) norbornylamine (1.3 moles, 0.48 g). Allowed to warm to room temperature during about 2 hours, stood 1 hour, added ethyl acetate (100 ml), evaporated to small volume. Residue subjected to column chromatography on silica gel using gradient elution with cyclohexane and ethyl acetate. The solvents were removed under reduced pressure to yield the desired product (e13) as a pale yellow oil.

I.r. spectrum as follows: 1802 cm$^{-1}$ (β-lactam C=O).
N.m.r. 0.9–3.7 (unassignable multiple peaks), 4.65 (1H,t, CH=), 4.97 (2H, C$_6$ H$_5$ CH$_2$), 5.1 (1H,s, 3-CH)

EXAMPLE 12 9-(N,N-dipropylamino)-9-deoxyclavulanic acid

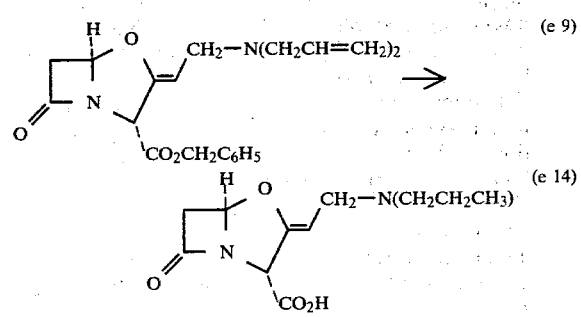

Benzyl 9-(N, N-diallylamino)-9-deoxyclavulanate (e9) was dissolved in ethanol (10 ml) and hydrogenolysed at room temperature and pressure using 10% Pd/C catalyst (70 mg). After filtration through kieselguhr the solvent was evaporated and the residue dissolved in ethyl acetate (25 ml) and the product extracted with water (3×10 ml). Evaporation in vacuo gave the zwitterion (e14) as a yellow gum in 85% yield.

(i.r. (film) 3400 (b), 2500 (b), 1790, 1695, 1625 cm$^{-1}$
n.m.r. (D$_2$O) 0.83 (6H, t, J 7 Hz N (CH$_2$ CH$_2$ CH$_3$)$_2$) 1.6 (4H, m, N(CH$_2$ CH$_3$)$_2$) 2.9 (5H, m, 6β-H, N(CH$_2$CH$_2$CH$_3$)$_2$) 3.25 (1H, dd, J 18 Hz, J$^1$ 3 Hz, 6 -H) 3.75 (2H, d, J 8 Hz, =CH.CH$_2$) 4.66 (1H, t,obscured by HOD peak, =CH CH$_2$) 4.95 1H, s,-5.72 (1H, d, J 3 Hz, 5-H).

EXAMPLE 13 9-[DL-N-Benzyl-N-(2-hydroxypropyl)amino]-9-deoxyclavulanic acid

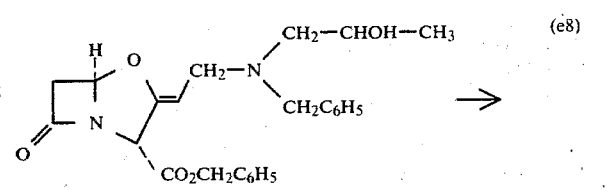

-continued

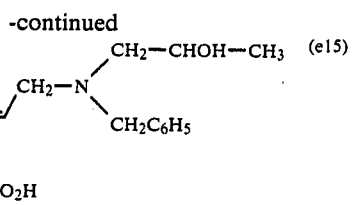

The zwitterion was prepared by hydrogenolysis of benzyl-9-[DL-N-benzyl-N-(2-hydroxypropyl)amino]-9-deoxyclavulanate (e 8) (90 mg) using 10% pd/C catalyst (33 mg) in ethanol (10 ml) at ambient temperature and pressure. The reaction was complete in 30 minutes. The catalyst was removed by filtration through kieselguhr and the filtrate was evaporated. The residual gum was taken up in ethyl acetate (20 ml) and extracted with water (4×10 ml). The aqueous extracts were combined and evaporated in vacuo to give the desired product (e15) as a pale yellow gum in 52% yield.

i.r. (film) 3400 (b) 1790, 1695, 1620 cm$^{-1}$.

The Field Desorption mass spectrum showed a peak at m/e 347 corresponding to (M+1) and a peak at m/e 165 (PhCH$_2$N+HCH$_2$CHOHCH$_3$).

EXAMPLE 14 Activity a. The compounds of this invention do not have a high level of acute toxicity, for example the compounds of Examples 8 and 12 have LD$_{50}$ values of greater than 500 mg/kg in mice when administered by the sub-cutaneous or oral routes.

b. The effectiveness of the compounds of this invention as synergists can be demonstrated by conventional MIC tests in which ampicillin alone, ampicillin and synergist and synergist alone are compared. The following test results were obtained using a strain of Staphylococcus aureus Russell which is neither inhibited by 250 μg/ml of ampicillin and nor inhibited by 5 μg/ml of synergist administered separately.

| Compound of Example No. | MIC of ampicillin (μg/ml) in presence of 1 μg/ml of synergist |
|---|---|
| 2 | 3.12 |
| 1 | 7.8 |
| 8 | <0.09 |
| 10 | 0.156 |

PREPARATION 1

General Procedure for Preparation of Sulphonate

The following process for the preparation of benzyl clavulanate —O— sulphonate trimethylamine salt (e1) may be adapted for the preparation of analogous esters by substituting the appropriate ester of clavulanic acid for (e1).

Benzyl clavulanate (57.8 mg) in dry dimethylformamide (0.8 ml) was treated with the trimethylamine-sulphur trioxide complex (55.6 mg) and left at ambient temperature for 18 hours. The solvent was removed in vacuo and the residue extracted with chloroform. The chloroform solution was evaporated and the residue was extracted several times with diethyl ether to remove benzyl clavulanate. The ether insoluble oil was shown to be the trimethylamine salt of benzyl clavulanate —O— sulphonate (e1) which was produced in 60% yield. (In the n.m.r. the —CH$_2$OSO$_3^-$ proton appeared at a doublet at about 4.71δ as compared to about 4.24δ in the starting material).

PREPARATION 2

General Procedure for Preparation of Diene Esters

The following process for the preparation of the benzyl ester of clavuladiene may be adapted to the preparation of other corresponding esters by replacing the benzyl clavulanate starting material by the corresponding ester of clavulanic acid.

Benzylclavulanate (0.2 g) was added to dry dimethylsulphoxide (6 ml) and dry benzene (3 ml) containing dicyclohexylcarbodiimide (0.43 g.). Anhydrous orthophosphoric acid (0.069 g) in dimethyl sulphoxide (2 ml) was added and the mixture stirred at room temperature for 4 hours. Thin layer chromatography showed a faster moving spot which gave a blue fluorescence at 366 n.m. The dicyclohexylurea was filtered off and benzene added to the filtrate, the organic phase was washed with water dried and evaporated. Fractionation on silica gel gave the product as a colourless oil in 71% yield. The diene was stored as a solution in acetone containing hydroquinone (0.01%) as a stabiliser.

I.r. (film): 1810, 1700, 1628, 1565 cm$^{-1}$

EXAMPLE 15 Methyl 2-(N-benzyl)norbonylaminodeoxyclavulanate

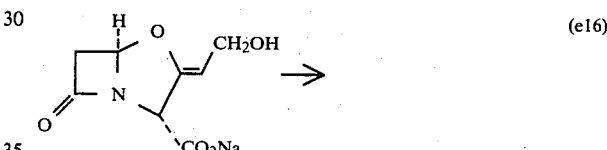

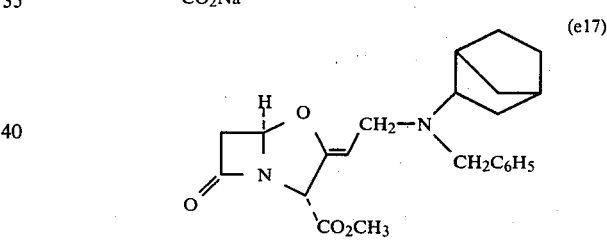

Sodium clavulanate tetrahydrate (e16) (2.9 g) in dimethylformamide (25 ml) was treated with iodomethane (25 ml) at room temperature over 1 hour. Acetontrile (10 ml) was added and removed by evaporation under reduced pressure (to remove excess methyliodide). The residual dimethylformamide solution was cooled in ice, and phthalic anhydride (1.5 g) and triethylamine (5 ml) added. After 1 hour at below 5° C., acetonitrile (2×25 ml portions) was added and evaporated under reduced pressure each time. 2-N-benzylnorbornylamine (4 g) was added and the reaction allowed to stir at 5° C. overnight. Most of the dimethylformamide was evaporated in vacuo. The residue was dissolved in 1:1 ethyl acetate-cyclohexane (100 ml), treated with silica gel (15 g) (chromatography grade), filtered off, evaporated to small bulk, and the residue subjected to gradient chromatography on silica gel using ethyl acetate and cyclohexane as eluents. The least polar β-lactam containing material was isolated by evaporation of the solvents from fractions containing it, to yield methyl 2-(N-benzyl)norbornylaminodeoxyclavulanate (e17) as a yellow oil (50 mg). It had I.r. 1800 (β-lactam) 1750 (ester C=O) 1695 cm$^{-1}$ (C=C).

EXAMPLE 16 Benzyl N-benzyl-N-ethylaminodeoxyclavulanate

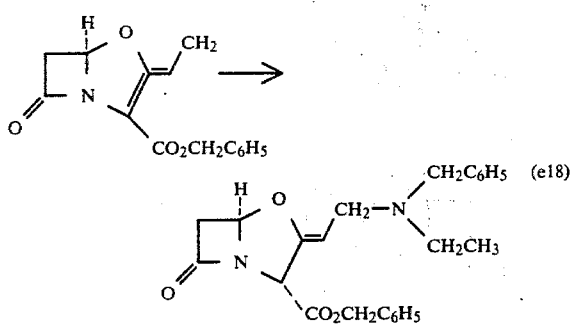

Clavudiene benzyl ester (0.44 g) in acetonitrile (8 ml) was cooled to −10° C. and treated with N-benzylethylamine (0.27 g). The reaction mixture was maintained at −5° to 0° C. for 1½ hours. Ethyl acetate (70 ml) was added and the mixture evaporated to small volume. The residue was subjected to column chromatography on silica gel using a gradient elution, starting with 7:1 cyclohexane/ethyl acetate increasing quickly to 2:1.

The material was collected in fractions just after the starting material. The solvents were evaporated to yield 45 mg of the title compound (e18) as a pale yellow oil. I.r. 1803 (β-lactam) 1750 (ester) 1700 (C=C) cm$^{-1}$.

What is claimed is:

1. A process for the production of a compound of the formula (II):

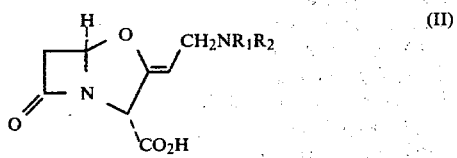

or an ester thereof of the formula (IV) or (V):

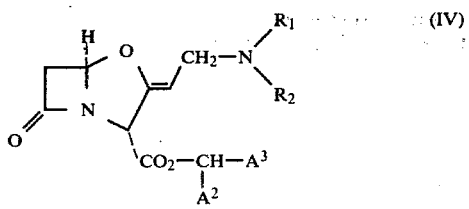

or

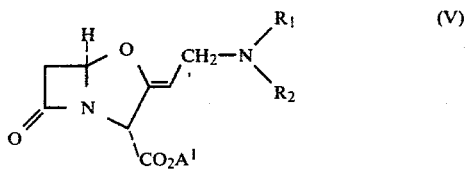

wherein $A^1$ is alkyl of 1–8 carbon atoms unsubstituted or substituted by halogen or a group of the formula $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen or by $A^5$ of $OA^5$ wherein $A^5$ is alkyl of up to 6 carbon atoms; and $A^3$ is phenyl unsubstituted or substituted by halogen or by $A^5$ of $OA^5$ wherein $A^5$ is as above defined; and wherein $R_1$ and $R_2$ are each independently a group of the sub-formula (a) (b) or (c):

(a) —$CR_4R_5R_6$
(b) —$CR_8R_9$—$C(R_{10})$=$CR_{11}R_{12}$
(c) —$CR_8R_9$—$CH(R_{10})$—$CHR_{11}R_{12}$ wherein $R_4$ is hydrogen; $R_5$ is hydrogen or alkyl of 1–4 carbon atoms; $R_6$ is phenyl unsubstituted or substituted by a substituent selected from the group consisting of halogen, OH, $OR_7$, $OCOR_7$, and $COR_7$, wherein $R_7$ is a hydrocarbon of up to 7 carbon atoms; $R_8$ is hydrogen or methyl; $R_9$ is hydrogen or methyl; $R_{10}$ is hydrogen or methyl; $R_{11}$ is hydrogen or methyl; or $R_{12}$ is hydrogen, alkyl of 1 to 4 carbon atoms or phenyl unsubstituted or substituted by a substituent selected from a group consisting of halogen, OH, $OR_7$, $OCOR_7$, $CO_2R_7$ and $COR_7$ wherein $R_7$ is a hydrocarbon of up to 7 carbon atoms which comprises reacting an amine of the formula $HN_1R_2$ (III) wherein $R_1$ and $R_2$ are as above defined, with a compound of the formula (X):

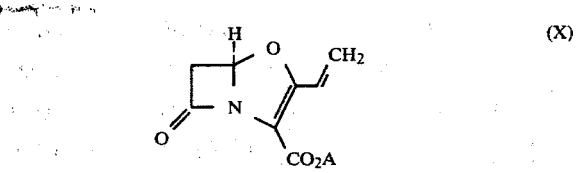

wherein $CO_2A$ is an ester as above defined and in the case of the acid, hydrogenating the ester produced to the corresponding acid.

2. A process according to claim 1 wherein compound (II) is of the formula:

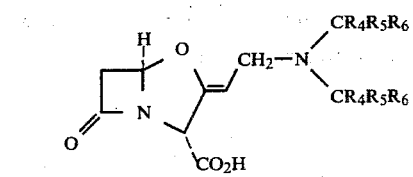

wherein $R_4$ is hydrogen, $R_5$ is hydrogen or alkyl of 1 to 4 carbon atoms and $R_6$ is phenyl unsubstituted or substituted by a substituent selected from the group consisting of halogen, alkyl of 1 to 4 carbon atoms, alkoxy of 1 to 4 carbon atoms or hydroxyl.

3. A process according to claim 2 wherein $R_5$ is hydrogen.

4. A process according to claim 2 wherein $CR_4R_5R_6$ is benzyl, methoxybenzyl or chlorobenzyl.

5. A process according to claim 1 wherein compound (II) is of the formula:

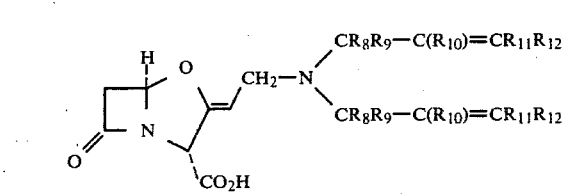

wherein each of $R_8$ to $R_{11}$ is independently hydrogen or methyl and $R_{12}$ is hydrogen, alkyl of 1 to 4 carbon atoms or phenyl unsubstituted or substituted by a substituent selected from the group consisting of halogen, alkyl of 1 to 4 carbon atoms, alkoxyl of 1 to 4 carbon atoms or hydroxyl.

6. A process according to claim 5 wherein each of $R_9$ to $R_{11}$ is hydrogen.

7. A process according to claim 6 wherein $R_{12}$ is hydrogen or alkyl of 1 to 4 carbon atoms.

8. A process according to claim 1 wherein compound (II) is of the formula:

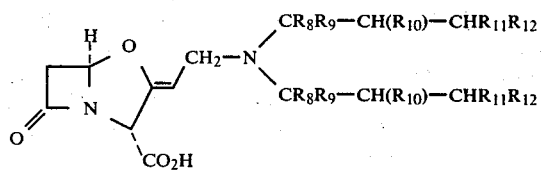

wherein each of $R_8$ to $R_{11}$ is independently hydrogen or methyl and $R_{12}$ is hydrogen, alkyl of 1 to 4 carbon atoms or phenyl unsubstituted or substituted by a substituent selected from the group consisting of halogen, alkyl of 1 to 4 carbon atoms, alkoxyl of 1 to 4 carbon atoms or hydroxyl.

9. A process according to claim 8 wherein each of $R_9$ to $R_{11}$ is hydrogen.

10. A process according to claim 9 wherein $R_{12}$ is hydrogen or alkyl of 1 to 4 carbon atoms.

11. A process according to claim 1 wherein compound (II) is of the formulae (VII) to (IX):

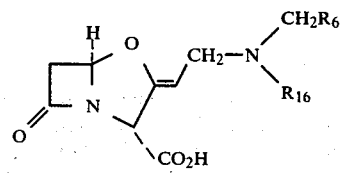

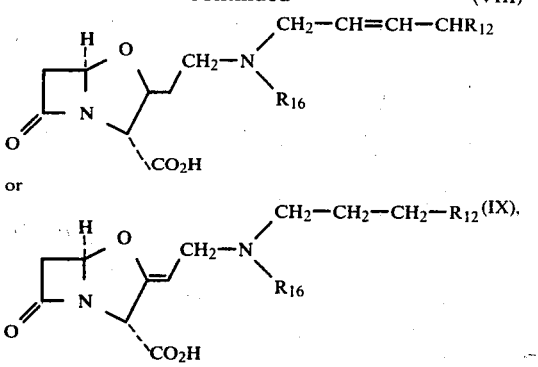

wherein $R_6$ is phenyl or phenyl mono-substituted by halogen, alkyl of 1 to 4 carbon atoms, alkoxyl of 1 to 4 carbon atoms or hydroxyl, $R_{16}$ is $CH_2R_6$, $CH_2CH=CHR_{12}$, $CH_2CH_2CH_2R_{12}$ or $CHR_{13}R_{14}$ wherein $R_6$ is as above defined, $R_{12}$ is alkyl of 1 to 4 carbon atoms, phenyl unsubstituted or mono-substituted by halogen, OH, alkyl, alkoxyl of 1 to 4 carbon atoms, or hydrogen, $R_{13}$ is hydrogen or alkyl of 1 to 4 carbon atoms, $R_{14}$ is alkyl of up to 14 carbon atoms unsubstituted or mono-substituted by OH, $OR_{15}$ or $COR_{15}$ wherein $R_{15}$ is alkyl, alkenyl, phenylalkyl or phenylalkenyl of up to 8 carbon atoms.

12. A process according to claim 1 wherein the ester is the phthalidyl, acetoxymethyl, pivaloyloxymethyl, α-acetoxyethyl, ethoxycarbonyloxymethyl or α-ethoxycarbonyloxyethyl ester.

13. A process according to claim 1 for production of the benzyl ester of the compound of the formula (II) wherein A is benzyl.

14. A process according to claim 1 wherein the reaction takes place in an aprotic solvent at a temperature of from $-10°$ C. to $+50°$ C.

15. A process according to claim 14 wherein the solvent is acetonitrile or dimethylformamide.

16. A process according to claim 14 wherein the temperature is from $-5°$ C. to $+25°$ C.

17. A process according to claim 1 wherein the temperature is from $0°$ C. to $20°$ C.

* * * * *

UNITED STATES PATENT AND TRADEMARK OFFICE
CERTIFICATE OF CORRECTION

PATENT NO. : 4,256,638
DATED : March 17, 1981
INVENTOR(S) : Ponsford et al.

It is certified that error appears in the above-identified patent and that said Letters Patent are hereby corrected as shown below:

On the cover sheet Insert:

-- (30) Foreign Application Priority Data

-- Oct. 13, 1975 [GB] United Kingdom.....41887/75 --.

Signed and Sealed this

Twenty-first Day of July 1981

[SEAL]

Attest:

GERALD J. MOSSINGHOFF

Attesting Officer

Commissioner of Patents and Trademarks